(12) United States Patent
Gaind et al.

(10) Patent No.: US 9,506,873 B2
(45) Date of Patent: Nov. 29, 2016

(54) PATTERN SUPPRESSION IN LOGIC FOR WAFER INSPECTION

(71) Applicant: KLA-Tencor Corporation, Milpitas, CA (US)

(72) Inventors: Vaibhav Gaind, Fremont, CA (US); Nisha Amthul, Milpitas, CA (US)

(73) Assignee: KLA-Tencor Corp., Milpitas, CA (US)

( * ) Notice: Subject to any disclaimer, the term of this patent is extended or adjusted under 35 U.S.C. 154(b) by 48 days.

(21) Appl. No.: 14/682,822

(22) Filed: Apr. 9, 2015

(65) Prior Publication Data

US 2015/0293035 A1    Oct. 15, 2015

Related U.S. Application Data

(60) Provisional application No. 61/979,522, filed on Apr. 15, 2014.

(51) Int. Cl.
| | | |
|---|---|---|
| *G01N 21/00* | (2006.01) | |
| *G01N 21/95* | (2006.01) | |
| *G01N 21/956* | (2006.01) | |

(52) U.S. Cl.
CPC ........ *G01N 21/9501* (2013.01); *G01N 21/956* (2013.01); *G01N 2201/10* (2013.01)

(58) Field of Classification Search
CPC ............................ G01N 21/00; G01N 21/956
USPC ...................................................... 356/237.5
See application file for complete search history.

(56) References Cited

U.S. PATENT DOCUMENTS

| | | | |
|---|---|---|---|
| 7,570,796 B2 | 8/2009 | Zafar et al. | |
| 7,676,077 B2 | 3/2010 | Kulkarni et al. | |
| 8,831,334 B2 | 9/2014 | Luo et al. | |
| 2006/0124874 A1* | 6/2006 | Uto | G01N 21/9501 250/559.45 |
| 2009/0257058 A1 | 10/2009 | Urano et al. | |
| 2010/0112730 A1 | 5/2010 | Brodsky et al. | |
| 2011/0170090 A1 | 7/2011 | Naftali et al. | |
| 2012/0268585 A1 | 10/2012 | Markwort et al. | |
| 2014/0009759 A1 | 1/2014 | Zhao et al. | |
| 2014/0016125 A1* | 1/2014 | Sullivan | G01N 21/9501 356/237.5 |
| 2015/0178907 A1 | 6/2015 | Zhang et al. | |

OTHER PUBLICATIONS

Written Opinion of the International Searching Authority for PCT/US2015/025920 mailed on Jun. 30, 2015.
International Search Report for PCT/US2015/025920 mailed on Jun. 30, 2015.

* cited by examiner

*Primary Examiner* — Roy M Punnoose
(74) *Attorney, Agent, or Firm* — Ann Marie Mewherter

(57) ABSTRACT

Methods and systems for detecting defects on a wafer are provided. One system includes an illumination subsystem configured to direct light to at least one spot on a wafer. The system also includes at least one element configured to block first portion(s) of light scattered from the at least one spot from reaching a detector while allowing second portion(s) of the light scattered from the at least one spot to be detected by the detector. The first portion(s) of the light are scattered from one or more patterned features in a logic region on the wafer. The second portion(s) of the light are not scattered from the one or more patterned features. The detector is not an imaging detector. The system further includes a computer subsystem configured to detect defects on the wafer based on output of the detector.

20 Claims, 2 Drawing Sheets

PATTERN SUPPRESSION IN LOGIC FOR WAFER INSPECTION

BACKGROUND OF THE INVENTION

1. Field of the Invention

This invention generally relates to methods and systems for pattern suppression in logic for wafer inspection.

2. Description of the Related Art

The following description and examples are not admitted to be prior art by virtue of their inclusion in this section.

Wafer inspection, using either optical or electron beam technologies, is an important technique for debugging semiconductor manufacturing processes, monitoring process variations, and improving production yield in the semiconductor industry. With the ever decreasing scale of modern integrated circuits (ICs) as well as the increasing complexity of the manufacturing process, inspection becomes more and more difficult.

In each processing step performed on a semiconductor wafer, the same circuit pattern is printed in each die on the wafer. Most wafer inspection systems take advantage of this fact and use a relatively simple die-to-die comparison to detect defects on the wafer. However, the printed circuit in each die may include many areas of patterned features that repeat in the x or y direction such as the areas of DRAM, SRAM, or FLASH. This type of area is commonly referred to as an array area (the rest of the areas are called random or logic areas). To achieve better sensitivity, advanced inspection systems employ different strategies for inspecting the array areas and the random or logic areas.

Inspecting the array areas tends to be simpler in some ways than inspecting random or logic areas. For instance, the array areas tend to include repeating, periodic patterned features. Therefore, removing the signals or data corresponding to such patterned features is relatively easy. For example, relatively small cells that have the same repeating patterned features may be compared to each other, signals and data from the patterned features will cancel each other out, and differences detected by such comparisons can be identified as potential defects. Since such cell-to-cell comparisons can be performed within a single die, the comparisons will not be affected by non-local noise sources such as process variations across the wafer. In addition, since patterned features in the array areas tend to repeat periodically across nearly an entirety of the array areas, signals or data corresponding to such patterned features can be removed relatively easily using, for example, Fourier filtering that can be performed optically or during image processing.

Since random or logic areas on wafers do not include such repeating, periodic features, the inspection approaches described above generally cannot be used for such areas. Instead, typically, inspection of random or logic areas is performed by using bright field imaging, in which specularly reflected light from the wafer is detected to form an image of the wafer in which the features in the random or logic areas are resolved. Since the features in such areas tend to not repeat on a regular basis within a die, images such as those described above that have been generated at the same within die position in multiple dies on the wafer are compared. Since the same patterns should be formed at the same within die position in multiple dies on the wafer, any differences detected by such comparisons may be identified as potential defects.

Such inspection of random or logic areas has, therefore, a number of disadvantages that make this inspection more difficult in some ways compared to array area inspection. For instance, bright field type inspection that is typically used for random or logic areas tends to be slower than dark field inspection and the optical requirements for bright field inspection systems tend to make such systems much more expensive than dark field inspection systems (e.g., due to the imaging capability required in such systems). In addition, since such inspection tends to rely on die-to-die comparisons of signals or data for defect detection, such inspection tends to be less sensitive than that achievable for array areas (e.g., due to non-local noise sources such as those described above). Furthermore, since the features formed in random or logic areas are not repeating and periodic in the same way that features formed in array areas are, eliminating the signals or data for non-defective features in random or logic areas is much more difficult than in array areas (e.g., since Fourier filtering is generally not possible).

Due to shrinking design rules as well as increasingly complex fabrication techniques, improvements in the sensitivity of random or logic area inspection will be required to keep pace with the technology. Accordingly, it would be advantageous to develop methods and systems for wafer inspection of random or logic areas that do not have one or more of the disadvantages described above.

SUMMARY OF THE INVENTION

The following description of various embodiments is not to be construed in any way as limiting the subject matter of the appended claims.

One embodiment relates to a system configured to detect defects on a wafer. The system includes an illumination subsystem configured to direct light to at least one spot on a wafer. The illumination subsystem includes at least one light source. The system also includes a scanning subsystem configured to cause the at least one spot to be scanned over the wafer. In addition, the system includes one or more detection channels. At least one of the one or more detection channels includes a detector configured to detect light scattered from the at least one spot on the wafer and to generate output responsive to the detected scattered light. The at least one detection channel also includes at least one element configured to block one or more first portions of the light scattered from the at least one spot from reaching the detector while allowing one or more second portions of the light scattered from the at least one spot to be detected by the detector. The one or more first portions of the light are scattered from one or more patterned features formed in a logic region on the wafer. The one or more second portions of the light are not scattered from the one or more patterned features. The one or more detection channels do not include any imaging detectors. The system further includes a computer subsystem configured to detect defects on the wafer based on the output. The system may be further configured as described herein.

Another embodiment relates to a method for detecting defects on a wafer. The method includes directing light to at least one spot on a wafer and scanning the at least one spot over the wafer. The method also includes blocking one or more first portions of light scattered from the at least one spot from reaching a detector while allowing one or more second portions of the light scattered from the at least one spot to be detected by the detector. The one or more first portions of the light are scattered from one or more patterned features formed in a logic region on the wafer. The one or more second portions of the light are not scattered from the one or more patterned features. The detector is not an imaging detector. In addition, the method includes detecting light scattered from the at least one spot on the wafer with the detector thereby generating output responsive to the detected scattered light. The method further includes detecting defects on the wafer based on the output.

Each of the steps of the method described above may be performed as described further herein. The method described above may include any other step(s) of any other method(s) described herein. The method described above may be performed using any of the systems described herein.

BRIEF DESCRIPTION OF THE DRAWINGS

Other objects and advantages of the invention will become apparent upon reading the following detailed description and upon reference to the accompanying drawings in which.

Figure 1:
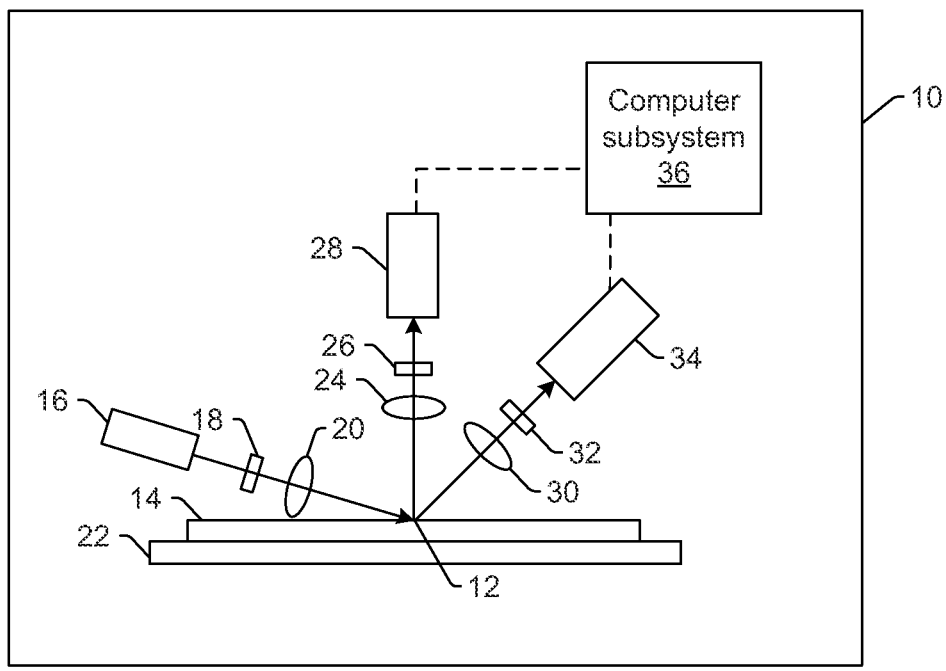
FIG. 1 is a schematic diagram illustrating a side view of one embodiment of a system configured to detect defects on a wafer.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects on a wafer. One embodiment of such a system is shown in FIG. 1. As shown in FIG. 1, system 10 includes an illumination subsystem configured to direct light to at least one spot 12 on wafer 14. The illumination subsystem includes at least one light source. For example, as shown in FIG. 1, the illumination subsystem includes light source 16. In one embodiment, the illumination subsystem is configured to direct the light to the at least one spot on the wafer at one or more angles of incidence that include at least an oblique angle of incidence. For example, as shown in FIG. 1, light from light source 16 is directed through optical element 18 and then lens 20 to spot 12 at an oblique angle of incidence. The oblique angle of incidence may include any suitable oblique angle of incidence, which may vary depending on, for instance, characteristics of the wafer and the defects to be detected on the wafer.

The illumination subsystem may be configured to direct the light to the wafer at different angles of incidence at different times. For example, the system may be configured to alter one or more characteristics of one or more elements of the illumination subsystem such that the light can be directed to the wafer at an angle of incidence that is different than that shown in FIG. 1. In one such example, the system may be configured to move light source 16, optical element 18, and lens 20 such that the light is directed to the at least one spot on the wafer at a different oblique angle of incidence or a normal (or near normal) angle of incidence.

The illumination subsystem may also or alternatively, in some instances, be configured such that the light can be directed to the at least one spot on the wafer at multiple angles of incidence simultaneously. In one such example, the illumination subsystem may include another light source (not shown), another optical element (not shown), and another lens (not shown) that are configured to direct light to the wafer at a different angle of incidence than that shown in FIG. 1. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s). The illumination subsystem may have any other suitable configuration known in the art for directing the light to the at least one spot at multiple angles of incidence sequentially or simultaneously.

In some such embodiments, the at least one light source includes at least one laser. For example, light source 16 shown in FIG. 1 may be a laser. The laser may include any suitable laser known in the art and may be configured to generate light at any suitable wavelength or wavelengths known in the art. In one example, the laser may be configured to generate light at a wavelength of 266 nm. In addition, the laser may be configured to generate light that is monochromatic or nearly-monochromatic. In this manner, the laser may be a narrowband laser. In another embodiment, the at least one light source includes only one or more narrowband light sources. In other words, the illumination subsystem preferably does not include any broadband light sources, which is advantageous as described further herein. The light source may also include light sources other than a laser, including other narrowband light sources.

In an additional embodiment, the illumination subsystem is configured to direct the light to two or more of the at least one spot on the wafer simultaneously. In other words, the system may be configured as a multi-spot inspection system. In one such embodiment, light from light source 16 may be a single light beam that is split into multiple light beams (not shown) by optical element 18, which may be configured as a diffractive optical element (DOE). Such an optical element may include any suitable DOE known in the art. The multiple light beams may then be focused onto wafer by lens 20. Although lens 20 is shown in FIG. 1 as a single refractive optical element, it is to be understood that, in practice, lens 20 may include a number of refractive and/or reflective optical elements that in combination focus the light from the DOE (or another element (not shown) included in the illumination subsystem) to the wafer.

In some instances, the multiple spots may form a one-dimensional (1D) array of illuminated spots on the wafer. However, the multiple spots may have any other spatial arrangement with respect to each other on the wafer. For instance, the multiple spots may form a two-dimensional (2D) array of spots on the wafer. Each of the illuminated spots may be spatially separated from each other and may otherwise preferably have the same characteristics (e.g., size, intensity, shape, etc.). Each of the illuminated spots may have a substantially small size on the wafer (e.g., dimensions of less than 0.5 um in both the x and y directions). The number of the multiple spots that are illuminated on the wafer simultaneously may vary depending on the configuration of the inspection system (e.g., from 2 spots to 20 spots). In addition, the number of the multiple spots that are used for inspection of any one wafer may vary depending on the type of inspection that is being performed and/or on the type of wafer that is being inspected.

The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection. For example, as described above, the system may be configured to alter one or more characteristics of the illumination subsystem to alter the angle of incidence used for inspection. The system may be configured to alter the illumination subsystem in a similar fashion to change one or more other characteristics (e.g., polarization, wavelength, etc.) of the illumination used for inspection.

The system also includes a scanning subsystem configured to cause the at least one spot to be scanned over the wafer. For example, the system may include stage 22 on which wafer 14 is disposed during inspection. The scanning subsystem may include any suitable mechanical and/or robotic assembly (that includes stage 22) that can be configured to move the wafer such that the at least one spot can be scanned over the wafer. In addition, or alternatively, the system may be configured such that one or more optical elements of the system perform some scanning of the at least one spot over the wafer. The at least one spot may be scanned over the wafer in any suitable fashion such as in a serpentine-like path or in a spiral path.

The system further includes one or more detection channels. At least one of the one or more detection channels includes a detector configured to detect light scattered from the at least one spot on the wafer and to generate output responsive to the detected scattered light. For example, the system shown in FIG. 1 includes two detection channels, one formed by collector 24, element 26, and detector 28 and another formed by collector 30, element 32, and detector 34. As shown in FIG. 1, the two detection channels are configured to collect and detect light at different scattering angles. In other words, both detection channels are configured to detect scattered light, and both detection channels are configured to detect light that is scattered at different angles from the wafer.

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the system that includes two detection channels, the system may include a different number of detection channels (e.g., only one detection channel or two or more detection channels). In one such instance, the detection channel formed by collector 30, element 32, and detector 34 may form one side channel as described above, and the system may include an additional detection channel (not shown) formed as another side channel that is positioned on the opposite side of the plane of incidence. Therefore, the system may include the detection channel that includes collector 24, element 26, and detector 28 and that is centered in the plane of incidence and configured to collect and detect light at scattering angle(s) that are at or close to normal to the wafer surface. This detection channel may therefore be commonly referred to as a "top" channel, and the system may also include two or more side channels configured as described above. As such, the system may include at least three channels (i.e., one top channel and two side channels), and each of the at least three channels has its own collector, each of which is configured to collect light at different scattering angles than each of the other collectors.

As described further above, each of the detection channels included in the system may be configured to detect scattered light. Therefore, the system shown in FIG. 1 is configured for dark field (DF) inspection of wafers. In addition, the system may not include any detection channels that are configured for bright field (BF) inspection of wafers. In other words, the system may not include any detection channel that is configured to detect light specularly reflected from the wafer. Therefore, the inspection systems described herein may be configured for only DF wafer inspection.

In one embodiment, the at least one of the one or more detection channels includes a collector configured to collect the light scattered from the at least one spot on the wafer, and the collector is not an imaging collector. For example, as described above, each of the detection channels may include its own collector (such as collectors 24 and 30 shown in FIG. 1), and each of the collectors may not be imaging collectors. In other words, the role of the collector(s) included in the system embodiments described herein is just to collect light, not image it onto any particular imaging plane. In this manner, the embodiments described herein are configured as spot scanning systems where both imaging axes are covered by the spot. In addition, although each of the collectors are shown in FIG. 1 as single refractive optical elements, it is to be understood that each of the collectors may include one or more refractive optical element(s) and/or one or more reflective optical element(s).

The one or more detection channels do not include any imaging detectors. In other words, each of the detectors included in the system is a non-imaging detector. In this manner, the detectors included in the system may be non-imaging detectors such as photo-multiplier tubes (PMTs) but not imaging detectors such as charge coupled devices (CCDs) and time delay integration (TDI) cameras. The detectors may also include any other suitable non-imaging detectors known in the art. In this manner, each of the detectors may be configured to detect certain characteristics of the scattered light such as intensity but may not be configured to detect such characteristics as a function of position within the imaging plane. As such, the output that is generated by each of the detectors included in each of the detection channels of the system may be signals or data, but not image signals or image data. Furthermore, it is to be understood that the detectors described herein are not configured as single light sensitive elements (e.g., pixels) in a multi-light sensitive element device (e.g., a CCD camera).

In instances in which the system is configured to direct light to multiple spots on the wafer simultaneously, the one or more detection channels may be configured to collect and detect light scattered from each of the multiple spots separately and simultaneously (i.e., separately with respect to space and simultaneously with respect to time). For example, the light scattered from all of the multiple spots may be separately and simultaneously collected by the collectors. In other words, one collector may be used to separately and simultaneously collect the light scattered from simultaneously illuminated spots on the wafer.

The detectors included in the detection channels may then be configured to separately and simultaneously detect the light collected from each of the spots. For example, each of the detection channels may include more than one detector (not shown in FIG. 1), and the number of detectors included in each of the detection channels may be equal to the number of simultaneously illuminated spots. The detection channels may then be configured such that the light collected separately from each of the spots is directed to only its corresponding detector. In this manner, each detection channel may include one collector that collects the light from all of the multiple spots separately and simultaneously and multiple detectors that separately and simultaneously detect the light collected from each of the spots. All of the detectors included in all of the detection channels may be non-imaging detectors. In other words, regardless of whether a detection channel of the system includes one detector or multiple detectors, each of the detector(s) is preferably a non-imaging detector.

The system embodiments described herein are therefore configured as non-imaging wafer inspection systems. In particular, as described further above, the illumination subsystem of the system is configured to direct light to at least one spot on the wafer and the at least one spot is relatively small in size. In addition, the collector(s) that are included in the detection channel(s) of the system are non-imaging, and the detector(s) that are included in the detection channel (s) are non-imaging. The system may therefore be commonly referred to as a "point imaging" system in that the spots that are illuminated on the wafer are small enough to be considered points and the light scattered from the spots is collected on a point-by-point basis. As described further above, the system is not configured such that the detector(s) of the detection channel(s) form images of the scattered light. However, as described further herein, a computer subsystem of the system may construct an image of an area on the wafer using the point-by-point non-imaging output of the detector(s). Therefore, although the system does not form images of the wafer optically, images of the wafer can be formed electronically. In addition, since the system does not form images of the wafer optically, the resolution of the system is defined by the at least one spot on the wafer, not the imaging capability of the collector(s) and/or detector(s).

The systems described herein are therefore different from other types of inspection systems in a number of important ways. For instance, some inspection systems are configured to illuminate a relatively large (e.g., tens of um) 2D area on a wafer and to detect light from that area as a function of position (i.e., to form an image of the light from the illuminated area). Such systems may be commonly referred to as "flood illumination" systems since a relatively large area on the wafer is "flooded" with light. Another type of inspection system is a 1D or line illumination system in which a relatively large (e.g., tens of um) 1D area on a wafer is illuminated and light is detected from that area as a function of position (i.e., to form an image of the light from the illuminated line). Therefore, unlike the system embodiments described herein, flood and line illumination type systems form images of wafers optically at the detector plane(s). Since the embodiments described herein are not configured for such illumination and imaging, the embodiments described herein have, as will be described further herein, a number of important advantages over these other types of inspection systems.

The embodiments described herein can also be described generally as narrowband laser scanning systems. The configuration of the systems described herein makes them particularly useful for high end line monitoring (HELM) applications as well $\leq 1\times$ nm design rule applications. For example, traditionally, laser-based inspection tools have demonstrated the best sensitivity in the array regions of dies on wafers, but with shrinking design rules combined with increasingly complex fabrication techniques, improved sensitivity of laser-based inspection tools is being demanded for logic regions of dies. To meet these demands, the embodiments described herein have been created. As described further herein, the embodiments are capable of meeting these demands by leveraging the light blocking elements described further herein, possibly in combination with advanced care area technology described further herein, to dramatically increase the sensitivity of laser-based inspection systems for inspection of both repeating and non-repeating logic structures.

The at least one of the one or more detection channels also includes at least one element configured to block one or more first portions of the light scattered from the at least one spot from reaching the detector while allowing one or more second portions of the light scattered from the at least one spot to be detected by the detector. The one or more first portions of the light are scattered from one or more patterned features formed in a logic region on the wafer, and the one or more second portions of the light are not scattered from the one or more patterned features.

The one or more patterned features from which scattered light is blocked may include any of the patterned feature(s) that are included in a logic region on a wafer. For example, in one embodiment, the one or more patterned features include one or more aperiodic patterned features. In another embodiment, the one or more patterned features include one or more non-repeating patterned features. In an additional embodiment, the one or more patterned features include one or more repeating patterned features.

In this manner, the at least one element that is configured as described above may be configured to suppress light scattered from patterned feature(s) formed in logic regions in output of the detector(s) and therefore images constructed from that output. For instance, if the light blocking element (s) described above are not included in the detection channel (s), then images constructed as described further herein from output of the detector(s) included in the detection channel(s) may include relatively intense light scattering from patterned feature(s) in the logic region. However, when the light blocking element(s) are included in the detection channel(s), images constructed as described further herein may include almost no light scattering from the patterned feature(s) in the logic region. The light blocking element(s) described herein are also capable of dramatically suppressing the light scattering from the patterned feature(s) in the logic region (e.g., on the order of 1000× or more in an image created using the system embodiments described herein without the light blocking element(s) compared to with the light blocking element(s)).

In this manner, in some embodiments, one or more characteristics of the at least one element are determined based on one or more characteristics of the one or more patterned features. For example, since the at least one element is configured to block light scattered from the patterned feature(s) and since the characteristics of the light scattered from the patterned feature(s) will vary depending on its/their characteristic(s), the characteristic(s) of the patterned features will determine the configuration of the at least one element. In this manner, by "learning" or determining the scatter of the logic features in the pupil plane of a detection channel, the scatter can be blocked as described further herein. The one or more characteristics of the at least one element may be determined in this manner empirically or experimentally.

In the empirical case, the characteristic(s) of the patterned features may be determined based on design data for the patterned feature(s), possibly with changes to the as-designed characteristics based on how the patterned feature(s) are expected to be formed on the wafer, which can be determined based on information about the process(es) used to form the features and/or a simulation of the process(es) used to form the features. Characteristic(s) of the patterned feature(s) as it/they will be formed on the wafer can then be used to determine expected light scattering from the patterned features. The expected light scattering with respect to a collector can then be used to determine the characteristic(s) of one or more light blocking elements that will be used for that collector. More specifically, once the light scattering of the patterned feature(s) has been determined with respect to a collector, the light blocking element(s) can be arranged in corresponding positions to thereby block such scattering.

Experimentally, the characteristic(s) of the light scattered from the patterned feature(s) can be determined, for example, by positioning an imaging device (e.g., a camera, not shown) in a pupil plane (not shown) of a collector of the system. The wafer may then be positioned such that the patterned feature(s) in the area of the logic region that is to be inspected are illuminated and/or scanned by the at least one spot. For example, NanoPoint (described further herein) may be used to determine where to go on a wafer (e.g., to one or more hot spots), and the imaging device can be used to measure the scattering at the location(s) on the wafer. The location(s) at which the measurements are performed may also be determined based on inspection results, which may include defect locations, for the wafer. Additional parameters of the system that will be used for inspection of the wafer or other similar wafers may also be determined. For example, an optics study may be performed to identify suitable illumination angle(s) and polarization(s). Once those parameters have been determined, then the scattering of the patterned logic feature(s) may be measured. The output of the imaging device (e.g., the scattering as a function of position) generated during such illumination and/or scanning may then be used to identify the scattered light corresponding to the patterned feature(s), e.g., based on patterns in the scattered light. Characteristic(s) of that identified scattered light may then be used to determine the characteristic(s) of the light blocking element(s). As such, measurements of the scattered light in the pupil plane may be used to determine the appropriate blocking configuration. In this manner, the at least one optical element may block the diffraction spots at the system's pupil plane.

The at least one element may be configured to block the one or more first portions of the light scattered from the patterned feature(s) in a number of different ways depending on the light scattered from the patterned feature(s). For example, a light blocking element may be configured to block light in an entire portion of its corresponding collector (e.g., one half of the front side or back side of the collector). In another example, a light blocking element may be configured to block two or more portions of its corresponding collector that are arranged in a 1D array (e.g., a series of lines in the light collected by the collector). In an additional example, a light blocking element may be configured to block two or more portions of its corresponding collector that are arranged in a 2D array (e.g., an array of spots in the light collected by the collector). Furthermore, a light blocking element may be configured to block light in a single area within its collector. For example, the light blocking element(s) may be configured to block a single line, spot, or area (having any 2D shape such as square, rectangular, circular, irregular, free form, or polygonal) within the collector.

The at least one element may have a variety of configurations depending on the types of light scattering that will be blocked. For example, the at least one element may include a set of opaque rods that can be individually moved into and out of an aperture depending on the light scattered from the patterned features. The individual rods may be moved into the aperture from one or more directions (e.g., from only one direction or in two opposing or perpendicular directions). In this manner, the at least one element may be a purely or fully mechanical blocking element. Other such mechanical blocking elements may also be used as the at least one element such as shutter(s) that can be used to partially block the collector. As such, the systems described herein may use a mechanical blocker to block the diffraction spots due to the patterned logic features.

The at least one element may also be configured to block the light scattered from the patterned feature(s) in a different way. For example, the at least one element may be configured as an electro-optical device (EOD), an acousto-optical device (AOD), or a micro-electro-mechanical system (MEMS) device. In one such example, the at least one element may be a liquid crystal display (LCD) device whose light blocking characteristics can be controlled and varied across a collector. In another such example, an AOD can be used to deflect light out of the optical path between a collector and its corresponding detector(s) in specific pattern(s) determined as described herein. In an additional such example, a MEMS device such as a micro-mirror array may be controlled and varied such that individual mirrors in the array can reflect light scattered from the patterned feature(s) out of the optical path between a collector and its corresponding detector(s).

In general, the at least one element may include any suitable element that can be used to block light scattered from patterned features such as those described herein and the at least one element used in systems such as those described herein may be selected by taking a number of factors into consideration such as the light scattering patterns that it will be used to block, how quickly the characteristics of the at least one element need to be changed, cost, etc.

In one embodiment, the system is configured to alter one or more characteristics of the at least one element based on one or more characteristics of the one or more patterned features. In other words, the element(s) that are configured as described herein to block light from patterned features are preferably alterable and therefore flexible. As such, the embodiments described herein are configured for pattern suppression in logic (random and repeating) areas using a flexible element that may be configured as a flexible aperture. In one such instance, if a light blocking element includes an aperture with a set of physical rods, then the characteristic(s) of the aperture can be customized using the physical rods to mask certain portions of the aperture for a variety of applications (e.g., nuisance, repeating pattern suppression, etc.).

In some embodiments, blocking of the scattered light from the one or more patterned features does not alter a resolution of the system. For example, in the embodiments described herein, the collector(s) are non-imaging collector(s), which is in contrast to optical imaging-based inspection systems where the imaging may be split between the illumination (e.g., in the x axis) and the collection (e.g., in the y axis). In contrast to such imaging-based systems, partially blocking the collector(s) as described herein has no impact on the resolution of the system, whereas on the imaging systems, partially blocking the collector impacts (i.e., reduces) resolution. In this manner, the non-imaging collector allows flexibility in the collection angles without any loss in resolution. For example, the light blocking element(s) described herein can be used to block repeating logic without any loss of resolution.

In one embodiment, the at least one element is not configured for Fourier filtering of the light scattered from the at least one spot due to the one or more patterned features. For example, current laser scanning tools (imaging based) have been using Fourier filtering to suppress repeating logic (with loss in resolution). However, Fourier filtering does not work for the patterned features described herein (e.g., random logic) since there are no periodic diffraction spots. In other words, since the patterned features that are located in the areas on the wafer being inspected are not periodic, the scattering from such features that is to be blocked by the at least one element described herein will not be periodic. As such, Fourier filtering cannot be used to block such scattering.

In some embodiments, the scanning subsystem is configured to cause the at least one spot to be scanned over only one or more portions of the logic region formed in one or more dies on the wafer. In one such embodiment, the one or more portions of the logic region correspond to micro care areas (MCAs) on the wafer. The care areas may be determined based on, for example, design information for the device being formed on the wafer. For example, the design information may be used to determine areas in the logic region that correspond to "hot spots" in the design. The "hot spots" can be generally defined as areas in a design that are of particular interest to a user for at least one reason such as that the areas are more susceptible to defects than other areas, the areas are more critical to proper device function than other areas, and the like. The care areas may be considered MCAs because of their substantially small size (e.g., having dimensions that are less than 1 um).

The MCAs may be determined, scanned, and inspected using the NanoPoint™ technology that is commercially available from KLA-Tencor, Milpitas, Calif. For example, NanoPoint can be used to help identify critical areas in a design that can impact yield and provide enhanced sensitivity for inspection. NanoPoint can also be used to draw substantially tiny care areas to identify critical regions and isolate them from regions that are noisier but less critical and are inspected with different thresholds than the critical areas. These substantially tiny critical areas may have logic features that contribute to noise but also have a specific scattering behavior. Therefore, as described further herein, using a training method, this scattering behavior can be determined and a light blocking element such as those described herein can be used to block the scatter from these features. Blocking the scatter will suppress the intensity from the noisy logic features relative to a defect and lead to enhanced defect capture. For example, after blocking the scatter from the patterned features, the intensity of the surrounding logic features will drop significantly relative to defects, thus significantly improving sensitivity.

NanoPoint training can, therefore, be performed on the relatively small critical care areas to block the scatter from logic features. For example, NanoPoint can be used to identify the care areas where defects could be located. The embodiments described herein may then be used to scan the care areas and record the scatter in the pupil plane of one or more collectors of the system. The light blocking element(s) may then be configured as described further herein to block where the scatter is the brightest.

The MCAs may also be determined, scanned, and inspected as described in commonly owned U.S. Pat. No. 7,570,796 issued on Aug. 4, 2009 to Zafar et al. and U.S. Pat. No. 7,676,077 issued on Mar. 9, 2010 to Kulkarni et al. and U.S. patent application Ser. No. 14/563,845 by Zhang et al. filed Dec. 8, 2014, and published at U.S Patent Application Publication No. 2015/0178907 on Jun. 25, 2015, all of which are incorporated by reference as if fully set forth herein. The embodiments described herein may be further configured as described in these patents and patent application.

In this manner, the embodiments described herein may be configured for pattern suppression in logic (random and repeating) using NanoPoint. In addition, as described above, the embodiments may be configured for pattern suppression in logic (random and repeating) using a flexible optical element (or flexible aperture). Therefore, the embodiments may be configured for pattern suppression in logic (random and repeating) using a flexible aperture in combination with NanoPoint. In addition, as described further herein, the embodiments may use multiple optical hardware components such as an oblique illumination subsystem, which decouples resolution from a collection aperture, and flexible aperture functionality as well as software components including image processing techniques such as NanoPoint.

The embodiments described herein can, therefore, be configured for MCA and/or NanoPoint assisted random logic suppression. Such configurations of the system embodiments provide a number of advantages over other currently used inspection systems. For example, the detection of defects in logic areas is significantly impacted by die-to-die process variation and other systematic noise sources. Using NanoPoint, the system may only inspect "hot spot" areas, which typically are as small as 1 um in size. The rest of the logic area, which can be a substantial source of noise, can be ignored. Currently used laser scanning inspection tools have been using Fourier filtering to suppress repeating logic. However, Fourier filtering does not work in random logic since there are no diffraction spots. Typically, the random logic structures are relatively large compared to defects that are being detected and, from scattering physics, we know that relatively big structures have a specific scattering behavior in a collector. Thus, using NanoPoint, the at least one element can be trained on a substantially small care area to block the scattered light from relatively big logic features. The at least one element can then suppress the intensity from the logic features relative to a defect.

Again, although the collector is being partially blocked, there is no impact on the resolution of the system due to the system architecture.

Another advantage of the embodiments described herein is that they allow laser scanning tools to become competitive in the logic inspection market. For example, since the embodiments described herein are configured to suppress the logic patterned features rather than resolving them, oblique incidence can be used in the embodiments described herein instead of normal incidence, which provides a significant advantage in throughput and therefore lower cost of ownership. In contrast, traditionally in logic inspection, inspection tools have been designed to resolve the logic patterns, which requires increasingly shorter wavelengths and higher resolutions due to the shrinking pattern sizes. As such, logic inspection is typically performed using broadband BF inspection tools. However, those types of inspection tools are typically much slower than laser-based DF inspection tools. Therefore, the embodiments described herein provide much higher throughput for logic inspection than that provided by currently used logic inspection systems.

An additional advantage is that, since the embodiments described herein are configured to suppress the scattering from the logic patterned features rather than resolving it, the embodiments described herein may be configured for relatively low resolution and relatively high throughput modes in logic. Therefore, the embodiments described herein do not need high numerical aperture (NA) lenses normally required for resolution purposes.

In another such embodiment, each of the one or more portions of the logic region is designed to have the same patterned features formed therein. For example, only portions of (or care areas in) the logic region that will have substantially the same patterned features formed therein (and therefore substantially the same light scattering due to the patterned features) may be inspected in a scan to avoid changing the at least one light blocking element during the scan. In this manner, if different types of hot spots are to be inspected in a logic region of a wafer, one type of hot spot may be inspected in one scan of the wafer and another type of hot spot may be inspected in another scan of the wafer, and one or more characteristics of the at least one blocking element may be altered between the scans. However, different types of hot spots may be inspected in one scan without changing the at least one blocking element during the one scan if the different types of hot spots will have substantially the same scattering from patterned features formed therein.

As described above, therefore, a scan of a wafer may include inspecting only one type of care area or hot spot in the logic region. However, the embodiments described herein may also be configured for inspection of multiple types of care areas or hot spots in the logic region in a single scan or a single inspection process. For example, in another embodiment, the scanning subsystem is configured to cause the at least one spot to be scanned over only one or more first portions of the logic region formed in one or more dies on the wafer and one or more second portions of the logic region formed in the one or more dies on the wafer. The one or more patterned features formed in the one or more first portions of the logic region have one or more characteristics that are different than one or more characteristics of the one or more patterned features formed in the one or more second portions of the logic region. The one or more characteristics of the patterned features in the different portions of the logic region may include any characteristics of the patterned features such as shape, dimensions, orientation, etc. that will affect the light scattering from the patterned features.

In such embodiments, the system may be configured to alter the at least one element depending on whether the one or more first portions of the logic region or the one or more second portions of the logic region are being scanned. For example, since the patterned features in the different portions of the logic region have different characteristic(s) as described above, the different portions will have different scattering characteristics in the pupil plane. Therefore, to substantially block the light from the patterned features in both of the different types of portions of the logic region, the characteristic(s) of the light blocking element(s) described herein will most likely have to be changed depending on which portion of the logic region is being inspected.

Changing the characteristic(s) of the light blocking element(s) depending on the portion of the logic area being scanned may be performed in a couple of different ways. For example, in one such embodiment, the one or more first portions of the logic region are scanned in the same pass as the one or more second portions of the logic region. In this manner, the characteristic(s) of the light blocking element(s) may be changed during a scan depending on which of the logic region portions are being scanned. In such embodiments, the configuration of the light blocking element(s) and the speed of the scanning may determine if this embodiment is practical. For example, the speed at which a fully mechanical light blocking element can be changed may be relatively slow compared to the scanning speed. Therefore, changing the configuration of such a light blocking element during a scan may necessitate a reduction in the scanning speed that is unacceptable to some users. However, other light blocking element(s) described herein such as EODs, AODs, and MEMS devices may be changed much more quickly than mechanical elements (e.g., at a rate approximating the scanning speed). Therefore, such light blocking elements can enable scanning of different types of care areas in a single scan without a reduction in throughput.

In another such embodiment, the one or more first portions of the logic region are scanned in one pass and the one or more second portions of the logic region are scanned in another pass. In this manner, different passes of the wafer may be performed, and different portions of the logic region may be inspected in the different passes. As such, one scan may be performed to inspect multiple instances of one type of logic care area, then another scan may be performed to inspect multiple instances of a different type of logic care area, and so on. Between the different passes, the configuration of the light blocking element(s) can be changed based on the expected patterned feature light scattering. Therefore, such an inspection may take a longer time than if different types of logic care areas can be inspected in the same scan, but such an inspection can be performed regardless of the speed at which the characteristic(s) of the light blocking element(s) can be changed.

The system also includes a computer subsystem configured to detect defects on the wafer based on the output. For example, as shown in FIG. 1, the system includes computer subsystem 36. Computer subsystem 36 is configured to acquire the output generated by detector(s) of the detection channel(s). For example, output generated by the detector(s) during scanning may be provided to computer subsystem 36. In particular, the computer subsystem may be coupled to each of the detector(s) (e.g., by one or more transmission media shown by the dashed lines in FIG. 1, which may include any suitable transmission media known in the art) such that the computer subsystem may receive the output generated by the detector(s). The computer subsystem may be coupled to each of the detectors in any other suitable manner.

The computer subsystem may be configured to detect the defects on the wafer in any suitable manner using any suitable defect detection method(s) and/or algorithm(s). For example, once the output has been generated by one or more detectors of one or more detection channels as described herein, the output may be used as input to any suitable method(s) and/or algorithm(s). In one example, one or more characteristics of the output such as intensity may be compared to a threshold and any of the output that has the one or more characteristics above the threshold may be identified as corresponding to potential defects while the output that does not have the one or more characteristics above the threshold may not be identified as corresponding to potential defects. Of course, many other defect detection methods and/or algorithms are possible and the method and/or algorithm that is used with the output may be selected and/or determined based on the characteristics of the output possibly in combination with characteristics of the wafer and/or defects of interest on the wafer.

In any case, since the scattered light from patterned logic features is substantially suppressed by the embodiments described herein and because the scatter from defects is typically non-uniform at the pupil plane, the defect scatter can be distinguished from logic feature scatter. In other words, since the patterned logic features and defects will scatter light differently and since the embodiments described herein are configured to block only light scattered from patterned logic features, the embodiments will detect light scattered from defects but not any or much scatter from patterned logic features. Therefore, the output generated by the embodiments described herein will be responsive to defects on wafers but will not be substantially responsive to patterned logic features.

For example, if the light blocking elements described herein are not included in the system, the diffraction spots from logic patterned features would be clearly seen in the pupil plane of the system. Therefore, images of the patterned logic features would be present in any images generated (as described further herein) from the non-imaging output of the system. In contrast, when the light blocking element(s) are included in the system and properly configured to block such diffraction spots, an image generated (as described further herein) from the non-imaging output of the system will not include images of the patterned features. Therefore, the intensity of the repeating logic features can be substantially or nearly completely suppressed in output generated using the light blocking element(s) described herein.

Thus, using the light blocking element(s) described herein removes unwanted wafer features from the constructed images. As such, the output will contain much less noise due to the patterned logic features. The light blocking element(s) described herein, therefore, help to enhance sensitivity to defects. In particular, the defect detection that is performed using the output of the embodiments described herein can be performed with higher sensitivity since the output will not be overwhelmed by noise that is erroneously detected as defects. Therefore, suppressing the diffraction spots using the light blocking element(s) described herein can significantly improve the sensitivity to defects in repeating logic patterns.

In some embodiments, the computer subsystem is configured to create at least one image of the logic region based on the output of the detector and to detect the defects on the wafer based on the at least one image, and the one or more patterned features cannot be resolved in the at least one image due to blocking of the one or more first portions of the light by the at least one element. For example, as noted above, the system is not configured to optically form images of the wafer. However, since the system may determine where on the wafer individual output was generated (e.g., based on information from the scanning subsystem), the individual output generated by one or more detectors may be "stitched together" based on that positional information to form an image of an area on the wafer that is larger than an area of the at least one spot on the wafer. Such image creation may be performed using any suitable method and/or algorithm known in the art of image processing.

Since the patterned feature scattering has been suppressed in the output generated by the system, the patterned feature scattering will be suppressed in any image generated using such output. As such, the images constructed by the computer subsystem will be substantially free of light scattering from the patterned features. Since the light scattering from the patterned features is typically relatively intense especially compared to the typical light scattering from defects, the images constructed in this manner will have a greater signal-to-noise ratio for defects. As such, patterned feature light scattering suppression in the images will enable much more sensitive defect detection than if the patterned feature light scattering was present in the images. The embodiments described herein can, therefore, be used to significantly boost the sensitivity of laser-based inspection systems in logic areas thereby providing the opportunity to increase adoption of such systems for HELM applications as well as other previously unexplored applications.

Once the images have been constructed as described above, defect detection may be performed using the images in any suitable manner using any suitable method(s) and/or algorithm(s). In other words, once the images have been created as described above, they can be treated in the same manner as any other images by defect detection methods and algorithms. The computer subsystem and the system may be further configured as described herein.

Figure 2:
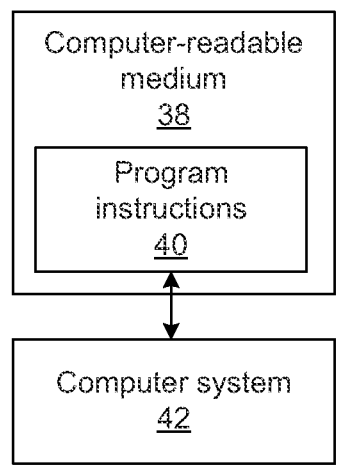
FIG. 2 is a block diagram illustrating one embodiment of a non-transitory computer-readable medium that includes program instructions executable on a computer system for performing one or more of the computer-implemented method embodiments described herein.

Another embodiment relates to a non-transitory computer-readable medium storing program instructions executable on a computer system for performing one or more steps of one or more methods for detecting defects on a wafer described herein. One such embodiment is shown in FIG. 2. For example, as shown in FIG. 2, computer-readable medium 38 stores program instructions 40 executable on computer system 42 for performing one or more steps of the methods described herein.

Program instructions 40 implementing methods such as those described herein may be stored on computer-readable medium 38. The computer-readable medium may be a storage medium such as a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

Computer system 42 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 3:
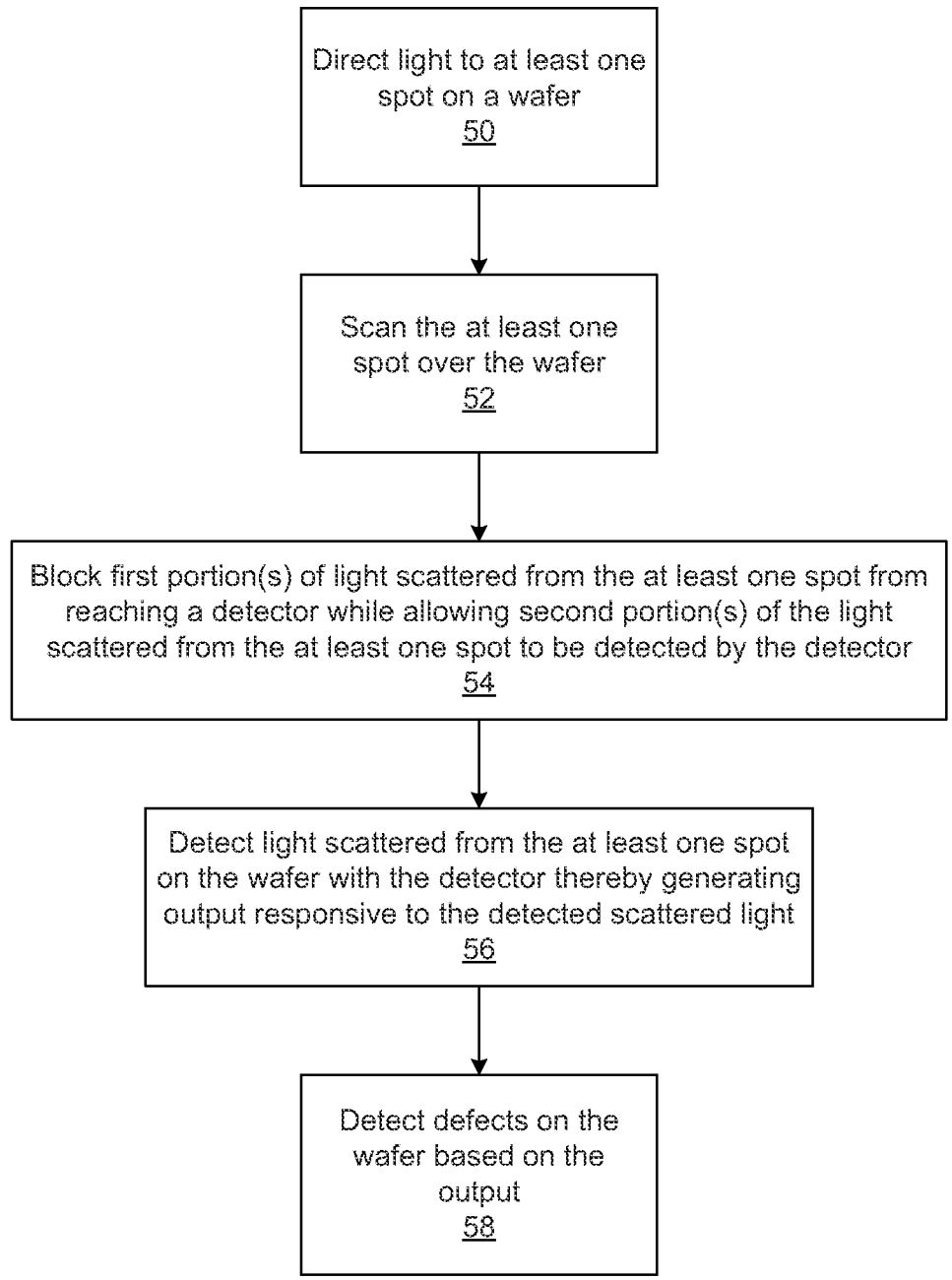
FIG. 3 is a flow chart illustrating one embodiment of a method for detecting defects on a wafer.

Another embodiment relates to a method for detecting defects on a wafer. One embodiment of such a method is shown in FIG. 3. As shown in step 50 of FIG. 3, the method includes directing light to at least one spot on a wafer, which may be performed according to any of the embodiments described herein. In addition, directing the light to the at least one spot may be performed using any of the illumination subsystems described herein. As shown in step 52 of FIG. 3, the method also includes scanning the at least one spot over the wafer, which may be performed according to any of the embodiments described herein. Scanning the at least one spot over the wafer may be performed using any of the scanning subsystems described herein.

As shown in step 54 of FIG. 3, the method includes blocking one or more first portions of light scattered from the at least one spot from reaching a detector while allowing one or more second portions of the light scattered from the at least one spot to be detected by the detector, which may be performed according to any of the embodiments described herein. Blocking the first portion(s) of the light while allowing the second portion(s) of the light to be detected may be performed using any of the at least one elements described herein. The one or more first portions of the light are scattered from one or more patterned features formed in a logic region on the wafer, and the one or more second portions of the light are not scattered from the one or more patterned features. The first and second portions of the light may be further configured as described herein. The detector is not an imaging detector and may be further configured as described herein.

As shown in step 56 of FIG. 3, the method further includes detecting light scattered from the at least one spot on the wafer with the detector thereby generating output responsive to the detected scattered light, which may be performed according to any of the embodiments described herein. Detecting the light may be performed using any of the detectors of any of the detection channels described herein. As shown in step 58 of FIG. 3, the method also includes detecting defects on the wafer based on the output, which may be performed according to any of the embodiments described herein. Detecting the defects may be performed using any of the computer subsystems described herein.

The methods described herein may also include storing results of any of the step(s) of any of the methods in a computer-readable storage medium. The results may include any of the results described herein and may be stored in any manner known in the art. The storage medium may include any suitable storage medium known in the art. After the results have been stored, the results can be accessed in the storage medium and used as described herein, formatted for display to a user, used by another software module, method, or system, etc.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a wafer, comprising:
   an illumination subsystem configured to direct light to at least one spot on a wafer, wherein the illumination subsystem comprises at least one light source;
   a scanning subsystem configured to cause the at least one spot to be scanned over the wafer;
   one or more detection channels, wherein at least one of the one or more detection channels comprises:
      a detector configured to detect light scattered from the at least one spot on the wafer and to generate output responsive to the detected scattered light; and
      at least one element configured to block one or more first portions of the light scattered from the at least one spot from reaching the detector while allowing one or more second portions of the light scattered from the at least one spot to be detected by the detector, wherein the one or more first portions of the light are scattered from one or more patterned features formed in a logic region on the wafer, wherein the one or more second portions of the light are not scattered from the one or more patterned features, and wherein the one or more detection channels do not comprise any imaging detectors; and
   a computer subsystem configured to detect defects on the wafer based on the output.

2. The system of claim 1, wherein the one or more patterned features comprise one or more aperiodic patterned features.

3. The system of claim 1, wherein the one or more patterned features comprise one or more non-repeating patterned features.

4. The system of claim 1, wherein the one or more patterned features comprise one or more repeating patterned features.

5. The system of claim 1, wherein the at least one element is not configured for Fourier filtering of the light scattered from the at least one spot due to the one or more patterned features.

6. The system of claim 1, wherein the scanning subsystem is further configured to cause the at least one spot to be scanned over only one or more portions of the logic region formed in one or more dies on the wafer.

7. The system of claim 6, wherein the one or more portions of the logic region correspond to micro care areas on the wafer.

8. The system of claim 6, wherein each of the one or more portions of the logic region is designed to have the same patterned features formed therein.

9. The system of claim 1, wherein the scanning subsystem is further configured to cause the at least one spot to be scanned over only one or more first portions of the logic region formed in one or more dies on the wafer and one or more second portions of the logic region formed in the one or more dies on the wafer, wherein the one or more patterned features formed in the one or more first portions of the logic region have one or more characteristics that are different than one or more characteristics of the one or more patterned features formed in the one or more second portions of the logic region, and wherein the system is further configured to alter the at least one element depending on whether the one or more first portions of the logic region or the one or more second portions of the logic region are being scanned.

10. The system of claim 9, wherein the one or more first portions of the logic region are scanned in the same pass as the one or more second portions of the logic region.

11. The system of claim 9, wherein the one or more first portions of the logic region are scanned in one pass and the one or more second portions of the logic region are scanned in another pass.

12. The system of claim 1, wherein the system is further configured to alter one or more characteristics of the at least one element based on one or more characteristics of the one or more patterned features.

13. The system of claim 1, wherein one or more characteristics of the at least one element are determined based on one or more characteristics of the one or more patterned features.

14. The system of claim 1, wherein the at least one of the one or more detection channels further comprises a collector configured to collect the light scattered from the at least one spot on the wafer, and wherein the collector is not an imaging collector.

15. The system of claim 1, wherein blocking of the scattered light from the one or more patterned features does not alter a resolution of the system.

16. The system of claim 1, wherein the computer subsystem is further configured to create at least one image of the logic region based on the output of the detector and to detect the defects on the wafer based on the at least one image, and wherein the one or more patterned features cannot be resolved in the at least one image due to blocking of the one or more first portions of the light by the at least one element.

17. The system of claim 1, wherein the illumination subsystem is further configured to direct the light to the at least one spot on the wafer at one or more angles of incidence comprising at least an oblique angle of incidence, and wherein the at least one light source comprises at least one laser.

18. The system of claim 1, wherein the at least one light source comprises only one or more narrowband light sources.

19. The system of claim 1, wherein the illumination subsystem is further configured to direct the light to two or more of the at least one spot on the wafer simultaneously.

20. A method for detecting defects on a wafer, comprising:
    directing light to at least one spot on a wafer;
    scanning the at least one spot over the wafer;
    blocking one or more first portions of light scattered from the at least one spot from reaching a detector while allowing one or more second portions of the light scattered from the at least one spot to be detected by the detector, wherein the one or more first portions of the light are scattered from one or more patterned features formed in a logic region on the wafer, wherein the one or more second portions of the light are not scattered from the one or more patterned features, and wherein the detector is not an imaging detector;
    detecting light scattered from the at least one spot on the wafer with the detector thereby generating output responsive to the detected scattered light; and
    detecting defects on the wafer based on the output.

* * * * *